United States Patent [19]

Kline

[11] 4,093,591

[45] June 6, 1978

[54] 3,5-DITERTIARY ALKYL-4-HYDROXYPHENYL (ALKYL) 6-ACYLOXY-4-THIA HEXANOATES AND HEXENAMIDES AS ANTIOXIDANTS

[75] Inventor: Richard H. Kline, Cuyahoga Falls, Ohio

[73] Assignee: The Goodyear Tire & Rubber Company, Akron, Ohio

[21] Appl. No.: 739,687

[22] Filed: Nov. 8, 1976

[51] Int. Cl.$^2$ .............................................. C08K 5/36
[52] U.S. Cl. ........................... 260/45.85 H; 526/312; 526/318
[58] Field of Search .............. 260/45.85 H, 45.85 R, 260/45.85 B, 45.85 A

[56] References Cited

U.S. PATENT DOCUMENTS

| | | | |
|---|---|---|---|
| 3,275,597 | 9/1966 | Mauz et al. | 260/45.85 H |
| 3,294,836 | 12/1966 | Peterson et al. | 260/45.85 H |
| 3,637,809 | 1/1972 | Kleiner | 260/45.85 H |
| 3,917,750 | 11/1975 | Knobloch | 260/45.85 R |
| 3,962,187 | 6/1976 | Kline | 260/45.85 R |
| 4,001,299 | 1/1977 | Dexter et al. | 260/45.85 B |

*Primary Examiner*—V. P. Hoke
*Attorney, Agent, or Firm*—D. B. Little; J. A. Rozmajzl

[57] ABSTRACT

Phenolic age resistors such as 4-(3,5-ditertiary butyl-4-hydroxyphenyl)-2-butyl 2-methyl-4-thia-6-octanoyloxy-hexanoate are used as antioxidants in diene rubbers, such as butadiene-styrene types and in polyolefins, such as polypropylene.

4 Claims, No Drawings

3,5-DITERTIARY ALKYL-4-HYDROXYPHENYL (ALKYL) 6-ACYLOXY-4-THIA HEXANOATES AND HEXENAMIDES AS ANTIOXIDANTS

BACKGROUND OF THE INVENTION

This invention relates to the preparation and use of phenolic age resistors for polymers, both unsaturated and saturated. More particularly, it concerns compounds comprised of a disubstituted phenolic group attached at the para position to a carbon chain containing sulfur, a carbonyl group, and a carboxylic ester moiety.

The use of sulfur-containing hindered phenols is known, e.g., see Canadian Pat. No. 904,339; U.S. Pat. Nos. Re. 27,004 and 3,590,083 and British Pat. No. 1,396,469.

The art disclosing hindered phenols is extensive, including those containing carbonyl or ester groups, see e.g., Japanese Pat. No. 27,735/68, U.S. Pat. No. 3,753,943; U.S. Pat. No. 3,810,929, Japanese Pat. No. 0468/63; *Rubber Chemistry and Technology*, Vol. 46, No. 1, Pp. 96–105, March, 1973; U.S. Pat. No. 3,714,122 and Canadian Pat. No. 812,262.

SUMMARY OF THE INVENTION

Among the objects of this invention are: (1) to provide phenolic antioxidants for the protection of polymers, (2) to provide polymers stabilized against oxidative degradation, and (3) to provide a process for the preparation of said antioxidants. Other objects and advantages will hereinafter appear.

The new compounds have the following general formula:

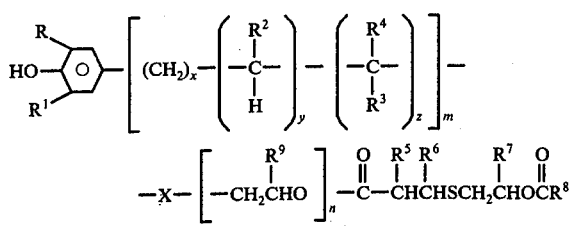

wherein R and $R^1$ are selected from the group consisting of tert. alkyl radicals having 4 to 8 carbons and cycloalkyl radicals having 5 to 12 carbons; $R^2$, $R^3$, $R^4$, $R^5$, $R^6$, $R^7$ and $R^9$ are selected from the group consisting of H and alkyl radicals having 1 to 4 carbons; $R^8$ is selected from the group consistng of alkyl radicals having 1 to 20 carbons, alkenyl radicals having 2 to 20 carbons, cycloalkyl radicals having 5 to 12 carbons, phenyl, substituted phenyl and aralkyl radicals having 7 to 12 carbon atoms; $x$, $y$ or $z$ equals 0 to 12; $x + y + z \leq 12$; $m$ equals 0 or 1; $n$ equals 0 to 3 and X is O or NH.

The term "substituted phenyl" as used herein means a phenyl ring to which is attached one or more radicals illustrated by but not limited to halogens such as chlorine, alkyl radicals such as methyl, and hydroxyl. Preferably the substituted phenyl radical contains one or two substituents selected from the group consisting of methyl and other lower alkyls.

These compounds can be used in free form to stabilize polymers against oxidative degradation, and those in which $R^8$ is 1-alkenyl can be used as polymerizable antioxidants in diene polymers.

DESCRIPTION OF THE PREFERRED EMBODIMENTS

The compounds of this invention are prepared by first reacting a β-mercaptoethanol of structure

with an unsaturated ester or amide of the structure

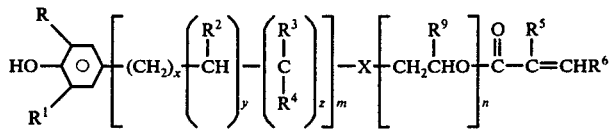

The products of this reaction which are of the structure

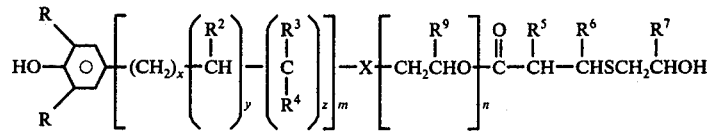

are then esterified by reaction with an acid chloride or anhydride derived from a carboxylic acid of the structure $R^8$COOH. The first reaction is normally carried out in a low boiling alcohol, in the presence of a catalytic amount of a base, such as an alkali metal hydroxide, a tertiary aliphatic amine, or a quaternary ammonium hydroxide at a temperature between room temperature and the boiling point of the solvent. The esterification is accomplished by adding an acid chloride or anhydride to a solution comprising the products of the first reaction; an acid acceptor, such as pyridine or triethylamine and an aprotic solvent, such as ethyl ether, tetrahydrofuran, or carbon tetrachloride. Equimolar amounts of acid chloride (or anhydride) and the alcohol are preferred. The reaction, which is mildly exothermic, is normally carried out at ambient temperature, but may be carried out at any temperature between 0° C. and the boiling point of the solvent.

A typical preparation of one of this new class of compounds is shown in Example I which is intended to illustrate and not limit the methods by which the compounds of the present invention are made. Unless otherwise indicated, all parts are parts by weight.

EXAMPLE I

A mixture of 12.5 grams of 3,5-ditert.butyl-4-hydroxyphenyl acrylate, 3.5 grams of 2-mercaptoethanol, 0.25 grams of potassium hydroxide, and 50 milliliters of ethanol was stirred at ambient temperature for 1½ hours. The reaction mixture was poured into water, and the oil which precipitated was separated by extraction with benzene. The benzene was removed on a rotary evaporator, leaving 16.0 grams of a viscous oil which was identified through its NMR spectrum as 3,5-ditert.butyl-4-hydroxyphenyl 6-hydroxy-4-thiahexanoate. This product, along with 9.1 grams of triethylamine, was dissolved in 50 milliliters of tetrahydrofuran. To this solution was added, over a period of 5 minutes, 5.7 grams of methacrylol chloride. During the addition, the temperature of the reaction mixture rose from 27° to 48° C. The reaction mixture was stirred for several hours and was then poured into water. The organic layer was separated by extraction with hexane. The hexane was removed on a rotary evaporator, leaving 17.2 grams of a viscous yellow oil, identified as 3,5-ditert. butyl-4-hydroxyphenyl 6-methacyloxy-4-thiahexanoate.

Typical examples of the radicals and substituents are:

(1) R and $R^1$ when tertiary alkyl radicals can be, for example, 1,1-dimethylpropyl; 1,1-dimethylbutyl; 1,1,2-trimethylpropyl; 1,1-dimethylpentyl; 1,1-dimethylhexyl; 1,1,3-trimethylpentyl; 1,1,3,3-tetramethylbutyl; 1-ethyl-1-methylbutyl; or tertiary butyl which is preferred;

(2) R,$R^1$ and $R^8$, when cycloalkyl radicals can be, for example, cyclopentyl; cyclohexyl; 2-methylcyclohexyl; 4-methylcyclohexyl; 2,4-dimethylcyclohexyl; 4-tertiary butylcyclohexyl; or 2-methylcyclopentyl;

(3) $R^2$, $R^3$, $R^4$, $R^5$, $R^6$, $R^7$ and $R^9$, when alkyl radicals can be for example, methyl (which is preferred), ethyl, n-propyl, isopropyl, n-butyl or isobutyl;

(4) $R^8$, when it is an alkyl radical can be, for example, those in number (3) above or pentyl, hexyl, octyl 2-ethylhexyl, decyl, undecyl, dodecyl, tridecyl, tetradecyl, hexadecyl, heptadecyl, octadecyl, or eicosyl;

(5) $R^8$, when it is a substituted phenyl can be, for example, p-tolyl; o-tolyl; p-ethylphenyl; p-isopropylphenyl; 2,4-xylyl; 3,5-xylyl; p-tert.butylphenyl; 2,4,6-trimethylphenyl; or 2,3,5-trimethylphenyl;

(6) $R^8$, when it is an aralkyl radical can be, for example, benzyl; 2-phenylethyl; p-methylbenzyl; 3-phenylpropyl; 2-phenylpropyl; p-tert.butyl benzyl; or 2,4-dimethylbenzyl; and (7) $R^8$, when it is an alkenyl radical can be, for example, vinyl and isopropenyl (preferred for polymerizable antioxidants); allyl, 1-propenyl, 2-butenyl, 1-hexenyl, 2-methyl-2-propenyl, 1-octenyl, 1-undecenyl, 3-methyl-1-heptenyl, 2-dodecenyl, 8-tridecenyl, 8-heptadecenyl or 5-nonadecenyl.

Polymers susceptible to oxidative degradation in which these antioxidants are beneficial include vulcanized and unvulcanized, saturated and unsaturated, natural and synthetic, homopolymers and copolymers. The term "copolymer" as used herein, means a polymer which is comprised of two or more different monomers. Representative examples of each type are given for illustrative purposes; natural rubber in its various forms, e.g., smoked sheet and balata; synthetic polymers including homopolymers (e.g., polyisoprene and polybutadiene), copolymers, e.g., styrene-butadiene rubbers, acrylonitrile-butadiene rubbers, and copolymers of propylene, ethylene and dicyclopentadiene. Polyolefins such as polypropylene and polyethylene are also illustrative of polymers which benefit by the practice of the present invention as are copolymers of ethylene and propylene.

Although the precise amount of antioxidant to be used depends on the polymer conditions to which it will be exposed, generally the amount employed varies between 0.001 and 10 parts by weight per 100 parts by weight of polymer. A preferred range is about 0.05 to 1.75. The compounds are especially useful in polypropylene at a level of about 0.1 parts per hundred as they possess superior resistance to discoloration by heat and ultraviolet light.

As free form antioxidants, the compounds of this invention may be added to the polymer in any of the conventional ways, such as by addition to the latex or to a solution of the polymer or by mixing with the dry polymer in a Banbury mixer or on a rubber mill.

The compounds can also be made to be an integral part of the polymer itself by either grafting or polymerization techniques. Being part of the polymer itself prevents the antioxidant from being volatilized or solvent extracted from the polymer.

The grafting technique is accomplished by combining the antioxidant and the polymer together in the presence of a free radical initiator. The form in which the polymer is grafted (e.g., solution, latex or dry form such as on a mill or in a Banbury) can depend upon the free radical initiator being used. Free radical initiators include redox systems, azo compounds and peroxides.

The polymerization method involves the use of the antioxidant as a monomer in a free radical polymerization reaction. The formation of the resulting oxidation resistant polymer takes place during the normal solution or emulsion polymerization reaction in which the principal monomers combine in the presence of catalyst, solvent, modifier, and whatever other emulsifiers and reagents are required for the preparation of the particular polymer. Conventional monomer systems and polymerization recipes and techniques are disclosed or referenced in U.S. Pat. No. 3,714,122. The weight ratio of polymerizable antioxidant to the sum of the other monomers ranges from about 0.01 to 5 parts by weight of antioxidant to 100 parts by weight of other monomers. The preferred range is about 0.1 to 2 parts by weight per 100 parts of other monomer. Preferably at least 50 parts by weight of the monomer system consists of a conjugated diene monomer such as 1,3-butadiene or isoprene.

Representative examples of the age resistors of this invention are:

1. 3,5-ditert.butyl-4-hydroxyphenyl 4-thia-6-methacryloxyhexanoate;

2. 3,5-ditert.butyl-4-hydroxyphenyl 3-methyl-4-thia-6-methacryloxyhexanoate;

3. 3,5-ditert.butyl-4-hydroxyphenyl 2-methyl-4-thia-6-benzoyloxyhexanoate;

4. 2-(3,5-ditert.butyl-4-hydroxybenzyloxy)ethyl 4-thia-6-methacryloxyhexanoate;

5. 4-(3,5-ditert.butyl-4-hydroxyphenyl)-2-butyl 4-thia-6-methacryloxyhexanoate;

6. 4-(3,5-ditert.butyl-4-hydroxyphenyl)-2-butyl 2-methyl-4-thia-6-octanoyloxyhexanoate;

7. N-(3,5-ditert.butyl-4-hydroxyphenyl)-2-methyl-4-thia-6-methacryloxyhexanamide;

8. N-(3,5-ditert.butyl-4-hydroxybenzyl)-4-thia-6-methacryloxyhexanamide;

9. N-[1,1-dimethyl-2-(3,5-ditert.butyl-4-hydroxyphenyl) ethyl]-2-methyl-4-thia-6-methacryloxyhexanamide;

10. N-[1,1-dimethyl-2-(3,5-ditert.butyl-4-hydroxyphenyl) ethyl]-4-thia-6-isobutyroxyhexanamide;
11. 2,2-dimethyl-3-(3,5-ditert.butyl-4-hydroxyphenyl)propyl 2-methyl-4-thia-6-acetoxyhexanoate;
12. 3,5-di-t-butyl-4-hydroxyphenyl 4-thia-6-stearoyloxyhexanoate;
13. 3,5-di-t-butyl-4-hydroxyphenyl 4-thia-6-oleoyloxyhexanoate;
14. 3,5-bis(1-methylcyclohexyl)-4-hydroxyphenyl 2-methyl-4-thia-6-acetoxyhexanoate;
15. 2-ethyl-2-butyl-3-(3,5-di-t-butyl-4-hydroxyphenyl)propyl 4-thia-6-acryloxyhexanoate;
16. 4-(3,5-di-t-butyl-4-hydroxyphenyl)-2-butyl 4-thia-6-(phenylacetoxy) hexanoate;
17. 4-(3,5-di-t-butyl-4-hydroxyphenyl)-2-butyl 4-thia-6-(4-methylbenzoyl) hexanoate.

For a better understanding of these complex structures, Table 1 is included, correlating the structures with the formulas of the example compounds:

Table 1

Correlation of Structure with Generic Formula

| Compound No. | n | m | X | R⁵ | R⁶ | R⁸ |
|---|---|---|---|---|---|---|
| 1 | 0 | 0 | 0 | H | H | $\mathrm{CH_3}$<br>$\mid$<br>$-\mathrm{C}=\mathrm{CH_2}$ |
| 2 | 0 | 0 | 0 | H | CH₃ | $\mathrm{CH_3}$<br>$\mid$<br>$-\mathrm{C}=\mathrm{CH_2}$ |
| 3 | 0 | 0 | 0 | CH₃ | H |  |
| 4 | 1 | 1 | 0 | H | H | $\mathrm{CH_3}$<br>$\mid$<br>$-\mathrm{C}=\mathrm{CH_2}$ |
| 5 | 0 | 1 | 0 | H | H | $\mathrm{CH_3}$<br>$\mid$<br>$-\mathrm{C}=\mathrm{CH_2}$ |
| 6 | 0 | 1 | 0 | CH₃ | H | —C₇H₁₅ |
| 7 | 0 | 0 | NH | CH₃ | H | $\mathrm{CH_3}$<br>$\mid$<br>$-\mathrm{C}=\mathrm{CH_2}$ |
| 8 | 0 | 1 | NH | H | H | $\mathrm{CH_3}$<br>$\mid$<br>$-\mathrm{C}=\mathrm{CH_2}$ |
| 9 | 0 | 1 | NH | CH₃ | H | $\mathrm{CH_3}$<br>$\mid$<br>$-\mathrm{C}=\mathrm{CH_2}$ |
| 10 | 0 | 1 | NH | H | H | —C(CH₃)₂ |
| 11 | 0 | 1 | 0 | CH₃ | H | CH₃ |
| 12 | 0 | 0 | 0 | H | H | —(CH₂)₁₆—CH₃ |
| 13 | 0 | 0 | 0 | H | H | H    H<br>$\mid$    $\mid$<br>—(CH₂)₇—C=C(CH₂)₇CH₃ |
| 14 | 0 | 0 | 0 | CH₃ | H | CH₃ |
| 15 | 0 | 1 | 0 | H | H | H<br>$\mid$<br>$-\mathrm{C}=\mathrm{CH_2}$ |
| 16 | 0 | 1 | 0 | H | H |  |
| 17 | 0 | 1 | 0 | H | H |  |

The following examples illustrate the use of the compounds of the present invention as antioxidants and are not intended to be limitations thereof.

In a test of some of these compounds as polymerizable antioxidants, butadiene/acrylonitrile/antioxidant terpolymers were prepared using the following recipe:

| Ingredient | Parts by Weight |
|---|---|
| Butadiene | 67 |
| Acrylonitrile | 33 |
| Water | 195 |

| Ingredient | Parts by Weight |
|---|---|
| Potassium soap of tallow fatty acids | 2.5 |
| Trisodium phospate | 0.2 |
| Ferrous sulfate | 0.0144 |
| Chelating agent* | 0.0568 |
| Sodium formaldehyde sulfoxylate | 0.0412 |
| Tert. dodecyl mercaptan | 0.5 |
| Cumene hydroperoxide (CHP)** | 0.023 |
| Polymerizable Antioxidant | 1.5 |

*90/10 mixture of tetrasodium salt of ethylenediaminetetraacetic acid and monosodium salt of N,N-di(α-hydroxyethyl)glycine.
**70% cumene hydroperoxide in cumene.

The resulting polymers were coagulated, extracted 48 hours with methanol in a Soxhlet extractor, dried, and dissolved in benzene. Films were cast from the benzene solutions and oxygen absorption measurements were made on the films. The results of these measurements are listed in Table 2.

Table 2

Oxygen Absorption of NBR (CHP Initiator) Containing Bound Antioxidant

| Compound | Hours to Absorb 1% O₂ at 100° C. |
|---|---|
| 1 | 65 |
| 2 | 97 |
| 4 | 80 |
| 5 | 38 |
| 7 | 265 |
| 8 | 151 |
| 9 | 149 |

Two butadiene/acylonitrile rubbers were prepared from monomer systems containing one of the compounds of the present invention. Azoiosbutyronitrile was used as the initiator. The polymers were extracted and oxygen absorption measurements made. The results are listed below:

Table 3

| Compound | Hours to Absorb 1% O₂ at 100° C. |
|---|---|
| 5 | 238 |
| 9 | 265 |

Table 4 contains additional data on samples of emulsion polybutadiene prepared from a monomer system containing 1.5 parts by weight of a polymerizable antioxidant per 100 parts by weight of butadiene.

Table 4

| Compound | Hours to Absorb 1% O₂ at 100° C. |
|---|---|
| 1 | 283 |
| 5 | 257 |
| 7 | 313 |
| 8 | 209 |
| 9 | 246 |

Compounds 1 through 11 were each used in free form to stabilize an SBR polymer (1006) by addition to a benzene solution of SBR-1006 at a concentration of 1 part per 100 parts rubber. Oxygen absorption tests were made on the films obtained by evaporation of the benzene. The testing procedure is of the type described in further detail in *Industrial and Engineering Chemistry*, Vol. 43, page 456 (1951) and *Industrial and Engineering Chemistry*, Vol. 45, p. 392 (1953).

Oven aging tests at 140° C. were also carried out on samples of polypropylene at 0.1 parts by weight free form antioxidant per 100 parts by weight polypropylene. The tests of the compounds used as free form antioxidants are presented in Table 5.

Table 5

| Compound | Hours to Absorb 1% Oxygen SBR-1006 | Days to Failure at 140° C. in Polypropylene |
| --- | --- | --- |
| 1 | 715 | — |
| 2 | 773 | — |
| 3 | 467 | 15 |
| 4 | 638 | — |
| 5 | 676 | 10 |
| 6 | 589 | 21 |
| 7 | 485 | 8 |
| 8 | 850 | — |
| 9 | 960 | — |
| 10 | 538 | 13 |
| 11 | 633 | — |
| Commercial Phenolic Antioxidant | — | 39 |

The antioxidants of this invention are equal or superior to commericially available products in discoloration characteristics. Several commercial controls and several of the compounds of this invention were mixed at the 0.1 pph level into polypropylene. Original color and color of the plastic after five days oven exposure at 140° C. was measured to test thermal discoloration resistance. The results are shown in Table 6.

Table 6

| Compound | Original Color | | | | Aged 5 days at 140° C. | | | |
| --- | --- | --- | --- | --- | --- | --- | --- | --- |
|  | Rd | a | b | CI* | Rd | a | b | CI* |
| No Antioxidant | 51.6 | −1.3 | +5.8 | 7.3 | Failed | | | |
| 3 | 53.3 | −1.7 | +5.6 | 7.3 | 51.1 | −1.6 | +5.3 | 7.0 |
| 5 | 55.3 | −1.2 | +6.0 | 7.7 | 53.5 | −1.3 | +5.7 | 7.6 |
| 6 | 53.0 | −1.4 | +6.2 | 7.0 | 53.2 | −1.5 | +6.6 | 6.6 |
| 7 | 53.0 | −1.5 | +7.5 | 5.9 | 48.1 | −1.5 | +10.8 | 3.9 |
| 10 | 53.2 | −2.8 | +4.5 | 4.5 | 49.7 | −3.5 | +12.8 | 3.8 |
| Commercial Phenolic Antioxidant Control 1 | 56.0 | −1.5 | +6.1 | 7.4 | 53.4 | −1.6 | +6.4 | 6.7 |
| Commercial Polycyclic Antioxidant Control 2 | 54.4 | −1.7 | +6.0 | 7.1 | 49.4 | −1.6 | +6.5 | 6.1 |
| Commercial Control 3 | 52.8 | −1.7 | +5.8 | 7.0 | 49.9 | −1.7 | +7.4 | 5.5 |
| Wingstay L | 52.7 | −1.7 | +7.5 | 5.7 | 43.7 | −4.4 | +30.6 | 1.2 |

*CI is Color Index

Three of the experimental antioxidants (3,5 and 6) were as good or better than the commercial controls, and all of them were superior to Wingstay L.

Ultraviolet light discoloration and stain tendencies were measured in an SBR based test formulation at the 1.5 pphr level. Measurements were taken of the original color of the rubber compounds and color after 120 hours Fade-O-Meter exposure both with and without a coating of white nitrocellulose lacquer on the samples. This lacquer manifests staining tendencies. The results of these discoloration tests are shown in Table 7.

Table 7

| Compound | Original Color Tinting | | | | Fade-O-Meter Exposed 120 hrs. discoloration | | | | Fade-O-Meter Exposed 120 hrs. - stain | | | |
| --- | --- | --- | --- | --- | --- | --- | --- | --- | --- | --- | --- | --- |
|  | Rd | a | b | CI* | Rd | a | b | CI* | Rd | a | b | CI* |
| No AO | 87.8 | −0.8 | +5.1 | 14.9 | 88.1 | −0.8 | +4.7 | 16.0 | 91.3 | −0.3 | +3.6 | 23.4 |
| 3 | 88.0 | −0.9 | +5.3 | 14.2 | 87.6 | −1.3 | +6.6 | 11.1 | 91.1 | −0.3 | +4.2 | 20.2 |
| 5 | 88.2 | −0.9 | +5.3 | 14.2 | 87.9 | −0.8 | +5.6 | 13.7 | 91.3 | −0.2 | +3.6 | 24.0 |
| 6 | 89.2 | −0.9 | +5.6 | 13.7 | 89.7 | −0.8 | +5.3 | 14.5 | 91.5 | −0.3 | +3.9 | 21.8 |
| 7 | 89.3 | −1.2 | +7.2 | 10.6 | 88.0 | −0.5 | +6.3 | 12.4 | 91.1 | −0.2 | +3.8 | 22.8 |
| 10 | 89.0 | −0.8 | +5.0 | 15.3 | 88.7 | −0.9 | +5.3 | 14.3 | 91.3 | −0.2 | +4.0 | 21.7 |
| Wingstay L Commercial Antioxidant | 87.6 | −0.9 | +6.1 | 12.5 | 87.3 | −1.3 | +7.2 | 10.3 | 91.2 | −0.3 | +4.0 | 21.2 |
| Control | 87.2 | −1.2 | +6.5 | 11.3 | 82.6 | −0.4 | +9.4 | 8.4 | **85.4 | −0.3 | 13.4 | 6.1 |

*CI is Color Index
**Visual stain at 48 hours

All of the experimental materials exceeded Wingstay L and the other control in discoloration resistance, and only compound 7 and the commercial control appeared to tint the original color slightly.

In Tables 6 and 7 color measurements are based on the Hunter Coordinate System in which an Rd of 100 is perfect reflectance and an Rd of 0 is a black body (perfect absorbance). Positive $a$ represents red; negative a green; positive $b$ yellow; and negative b blue. The greater the absolute value of $a$ or $b$, the greater is the intensity of color.

Color Index is $Rd/(|a| + |b|)$. The greater the color index, the closer color is to white.

The preferred reaction temperature for the reaction between the unsaturated ester or amide and the $\beta$-mercaptoethanol depends on the particular ester or amide used. Generally, the reaction proceeds well at the reflux temperature of the solvent (78° C. in the case of ethanol). The amount of base used is generally less than five moles per 100 moles of reactants, preferably less than one mole per 100 moles of reactants. The two reactants are preferably present in stoichiometric amounts, i.e., equimolar, although other ratios can be utilized.

Examples of unsaturated esters and amides which can be used in the first reaction are:

3,5-ditert.butyl-4-hydroxyphenyl acrylate
3,5-ditert.butyl-4-hydroxyphenyl 2-butenoate
3,5-ditert.butyl-4-hydroxyphenyl methacrylate
3,5-ditert.butyl-4-hydroxyphenyl methacrylamide
3,5-ditert.butyl-4-hydroxyphenyl acrylamide Examples of the solvents which may be used are: ethanol, methanol and 1-propanol.

Examples of the bases which may be used are: potassium hydroxide, sodium hydroxide, triethylamine, and trimethyl benzyl ammonium hydroxide.

The acid acceptor in the esterification reaction is used in amounts equimolar with the acid chloride, although some excess can be used. Equimolar amounts of acid chloride (or anhydride) and the alcohol are preferred, although different ratios may be used and a 10 percent excess of acid chloride over the equimolar amount is sometimes desirable.

Examples of acid chlorides and anhydrides which may be used are acetic anhydride; acetyl chloride, methacryloyl chloride; isobutyryl chloride; acryloyl chloride; methylbenzoyl chloride and benzoic anhydride.

While certain representative embodiments and details have been shown for the purpose of illustrating the invention, it will be apparent to those skilled in this art that various changes and modifications may be made therein without departing from the spirit or scope of the invention.

What is claimed is:

1. A composition of matter stabilized against oxidative degradation which is comprised of:
   A. a polymer susceptible to oxidative degradation selected from the group consisting of natural rubber, homopolymers wherein the monomer is selected from the group consisting of mono-olefin monomers and diolefin monomers, and synthetic copolymers wherein at least one of the monomers is selected from the group consisting of monoolefin monomers and diolefin monomers; and
   B. from 0.001 to 10 parts by weight of the anti-oxidant having the following structural formula:

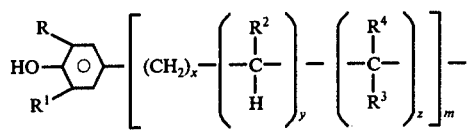

-continued

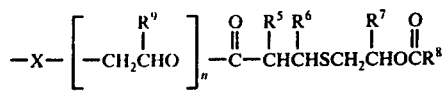

wherein R and $R^1$ are radicals selected from the group consisting of tert. alkyl radicals having from 4 to 8 carbons, and cycloalkyl radicals having from 5 to 12 carbons; $R^2$ and $R^3$ are selected from the group consisting of H, and alkyl radicals having from 1 to 4 carbons; $R^4$, $R^5$, $R^6$, $R^7$ and $R^9$ are selected from the group consisting of H and alkyl radicals having from 1 to 4 carbons; $R^8$ is selected from the group consisting of alkyl radicals having from 1 to 20 carbons, alkenyl radicals having from 12 to 20 carbons, cycloalkyl radicals having from 5 to 12 carbons, phenyl, substituted phenyl, and aralkyl radicals having from 7 to 12 carbon atoms; $x$, $y$ or $z$ equals 0 to 12; $x + y + z \leq 12$; $m$ equals 0 or 1; $n$ equals 0 to 3; and X is O or NH per 100 parts by weight of polymer.

2. The composition of claim 1 wherein the polymer is polypropylene and the antioxidant is used in the ratio of 0.05 to 1.75 parts by weight of antioxidant per 100 parts by weight of polypropylene.

3. The composition of claim 2 wherein the antioxidant is 4-(3,5-ditert.butyl-4-hydroxyphenyl)-2-butyl 2-methyl-4-thia-6-octanoyloxyhexanoate.

4. The composition of claim 2 wherein the antioxidant is 3,5-ditert.butyl-4-hydroxyphenyl 2-methyl-4-thia-6-benzoyloxyhexanoate.

* * * * *